United States Patent [19]

Manning

[11] Patent Number: 5,437,633
[45] Date of Patent: * Aug. 1, 1995

[54] SELECTIVE AORTIC ARCH PERFUSION

[75] Inventor: James E. Manning, Chapel Hill, N.C.

[73] Assignee: The University of North Carolina at Chapel Hill, Chapel Hill, N.C.

[ * ] Notice: The portion of the term of this patent subsequent to Jun. 1, 2010 has been disclaimed.

[21] Appl. No.: 211,374

[22] Filed: Mar. 30, 1994

[51] Int. Cl.⁶ .............................. A61M 31/00
[52] U.S. Cl. ..................... 604/53; 128/898; 514/716; 514/718
[58] Field of Search ............... 604/53; 128/898; 514/772, 832, 728, 716, 718

[56] References Cited

U.S. PATENT DOCUMENTS

| | | | |
|---|---|---|---|
| 3,962,439 | 6/1976 | Yokoyama et al. | |
| 4,686,085 | 8/1987 | Osterholm | 604/21 |
| 5,085,630 | 2/1992 | Osterholm | 604/28 |
| 5,216,032 | 6/1993 | Manning | 514/718 |
| 5,334,142 | 8/1994 | Paradis. | |

FOREIGN PATENT DOCUMENTS 1076119 8/1982 U.S.S.R. .

OTHER PUBLICATIONS

R. J. Novick, et al.; *Protection of the hypertrophied pig myocardium,* Journal of Thoracic and Cardiovascular Surgery 89 pp. 547–566, (1985).
C. S. Goodman and A. Gilman; *the Pharmacological Basis of Therapeutics,* Macmillan Publishing Company Seventh Edition pp. 716–718 (1985).
SU, A., Mosc. Medical Inst. Abstract 28 Feb. 1984.
G. B. Martin et al.; *Aortic and Right Atrial Pressures During Standard and Simultaneous Compression and Ventillation CPR in Human Beings,* Annals of Emergency Medicine pp. 125/37–130/42 (Feb. 1986).
M. Cleman, et al.; *Prevention of ischemia during precutaneous transluminal coronary angioplasty by transcatheter infusion of oxygenated Fluosol DA 20%,* Therapy and Prevention Coronary Angioplasty 74, pp. 555–562 (1986).
A. Martin, et al.; *Physical Chemical Principles in the Pharmaceutical Science, Physical Pharmacy,* pp. 276–277 (1988).
The Merck Index, Eleventh Edition (1989).
A. K. Bajaj, et al; *Limitation of Myocardial REperfusion Injury by Intravenous Perfluorochemicals,* Circulation 79, pp. 645–656 (1989).
C. L. Emerman, et al; *Hemodynamic Effects of the Intra–aortic Balloon Pump During Experimental Cardiac Arrest,* Am. J. Emerg. Med. 7 (1989).
H. Memezawa et al.; *Effects of Fluosol-DA on Brain Edema, Energy Metabolites, and Tissue Oxygen Content in Acute Cerebral Ischemia,* Advances in Neurology 52, pp. 109 –118 (1990).
L. B. Becker et al.; *Outcome of CPR in a Large Metropolitan Area-Where are the Survivors?,* Annals of Emergency Medicine, pp. 48/355–54/361 (1990).
J. E. Manning et al; *Selective Aortic Arch Perfusion During Cardiac Arrest: Rapid Aortic Arch Pressurization is Required to Consistently Achieve Competent Aortic Valve Closure and Coronary-Perfusion,* Abstract.

Primary Examiner—C. Fred Rosenbaum
Assistant Examiner—Chalin Smith
Attorney, Agent, or Firm—Bell, Seltzer, Park & Gibson

[57] ABSTRACT

A method of treating a subject in cardiac arrest, comprises blocking the descending aorta of the subject and then perfusing the aortic arch of the subject with a protective solution. The protective solution is one capable of delivering oxygen to the heart of said subject, such as a perfluorochemical blood substitute. Following perfusion, spontaneous circulation is restored.

In an improved embodiment of the foregoing, a vasoconstrictor such as epinephrine is administered concurrently with the perfusing step in an amount effective to enhance coronary perfusion with said protective solution.

20 Claims, 4 Drawing Sheets

SELECTIVE AORTIC ARCH PERFUSION

This invention was made with government support under USPHS General Research Support Award 5-SO1-FR-05406. The government has certain rights to this invention.

FIELD OF THE INVENTION

The present invention relates to a method of treating patients in cardiac arrest.

BACKGROUND OF THE INVENTION

When a person suffers a cardiac arrest either inside or outside the hospital, the chances of survival are small. See L. Becker et al., *Ann. Emerg. Med.* 20, 355–361 (1991). One of the major reasons for this poor outcome is the fact that chest compression during basic cardiopulmonary resuscitation (CPR) results in little forward blood flow. Though certain drugs, like epinephrine, have been shown to improve vital organ blood flow during CPR, they are given almost exclusively into a vein and therefore, must slowly circulate to the heart, through the heart and lungs, and finally to the peripheral arteries where their major beneficial effects occur. During this circulation time, the heart and brain continue to receive blood flow which cannot sustain cellular survival. Invasive techniques such as open-chest cardiac massage (OCCM), direct mechanical ventricular assistance (DMVA), and cardiopulmonary bypass (CPB) provide better vital organ blood flow. See generally R. Bartlett et al., *Ann. Emerg. Med.* 13 (Part 2), 773–777 (1984); M. Anstadt et al., Resuscitation 21, 7–23 (1991); P. Safar et al., *Am. J. Emerg. Med.* 8, 55–67 (1990). However, adapting these techniques for widespread use in the pre-hospital setting seems unlikely. In most cases, the window of time allowing for good neurologic recovery would likely run out before these techniques could be employed in the emergency department.

The inventions disclosed herein are based upon ongoing research into means by which the survival rates of sudden, out-of-hospital, cardiac arrest may be increased.

SUMMARY OF THE INVENTION

The hypothesis that a less invasive technique enhancing cardiac activity and preserving neuronal integrity might improve survival and be adaptable to the pre-hospital care setting led to the development of the new technique disclosed herein, termed selective aortic arch perfusion. The purpose of this technique is to substantially isolate the coronary and (preferably) cerebral circulations for perfusion with an oxygenated solution. Such infusion promotes return of spontaneous circulation (ROSC), typically using other standard life support measures such as defibrillation.

In accordance with the foregoing, a method of treating a subject in cardiac arrest comprises blocking the descending aorta of the subject; and then perfusing the aortic arch of the subject with a protective solution, which protective solution is capable of delivering oxygen to the heart of the subject (i.e., to the cardiac muscle through the coronary arteries). The protective solution is perfused in an amount sufficient to enhance cardiac electrical activity. This method is herein referred to as selective aortic arch perfusion, or "SAAP". Spontaneous circulation is restored after the perfusing step.

Also disclosed herein is an improvement upon the foregoing method, in which the subject is administered a vasoconstrictor concurrently with the perfusing step, the vasoconstrictor being administered in an amount effective to enhance coronary perfusion with the protective solution.

To simplify explanation and definition of the inventions disclosed herein, the delivery of protective solution is discussed with reference to cardiac tissue. Those skilled in the art will recognize, however, that a benefit of the foregoing is that brain cells can be oxygenated by perfusion through the carotid arteries during selective aortic arch perfusion when the aorta is blocked distal to the carotid arteries (as is preferably the case). Thus, the protective solution is delivered to the brain tissue in like manner as it is delivered to cardiac tissue.

Also disclosed herein is the use of a vasoconstrictor for the preparation of a medicament for enhancing coronary perfusion with a protective solution during selective aortic arch perfusion.

Also disclosed herein is a protective solution useful for selective aortic arch perfusion, which protective solution is a physiologically acceptable solution capable of carrying oxygen, and which contains a vasoconstrictor in an amount sufficient to enhance coronary perfusion with said protective solution during selective aortic arch perfusion.

The foregoing and other aspects and improvements upon the present invention are explained in detail in the specification set forth below and the accompanying drawings.

DETAILED DESCRIPTION OF THE INVENTION

The term "cardiac arrest" as used herein, refers to all types of cardiac arrest, including ventricular fibrillation, asystole, and electrical-mechanical dissociation. The methods disclosed herein are particularly advantageously employed on subjects in cardiac arrest due to ventricular fibrillation.

Blocking of the descending aorta, and infusion into the aortic arch, may be carried out with a balloon catheter configured to be inserted into the femoral artery, with the balloon positioned to block the descending aorta. The balloon is preferably positioned distal to the carotid arteries, and may also be positioned distal to the left subclavian artery, but is preferably located at least proximal to the renal arteries, and more preferably within the chest (i.e., above the diaphragm).

Figure 1:
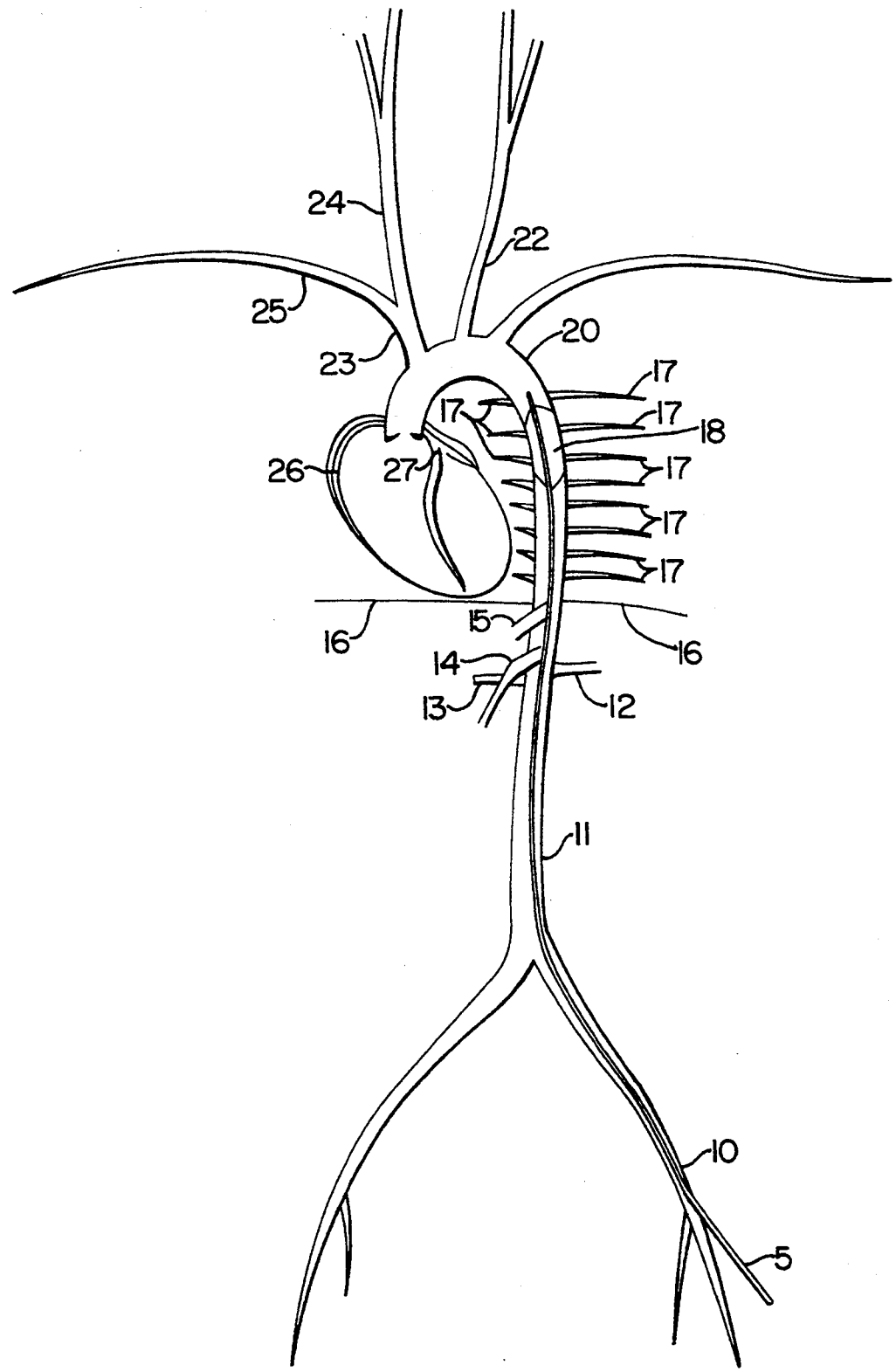
FIG. 1 is a schematic diagram of a balloon catheter inserted through the femoral artery into the aorta in a human subject proximal to the diaphragm but distal to the left common carotid artery, with the balloon inflated to block the descending aorta and perfuse the aortic arch.
Figure 2:
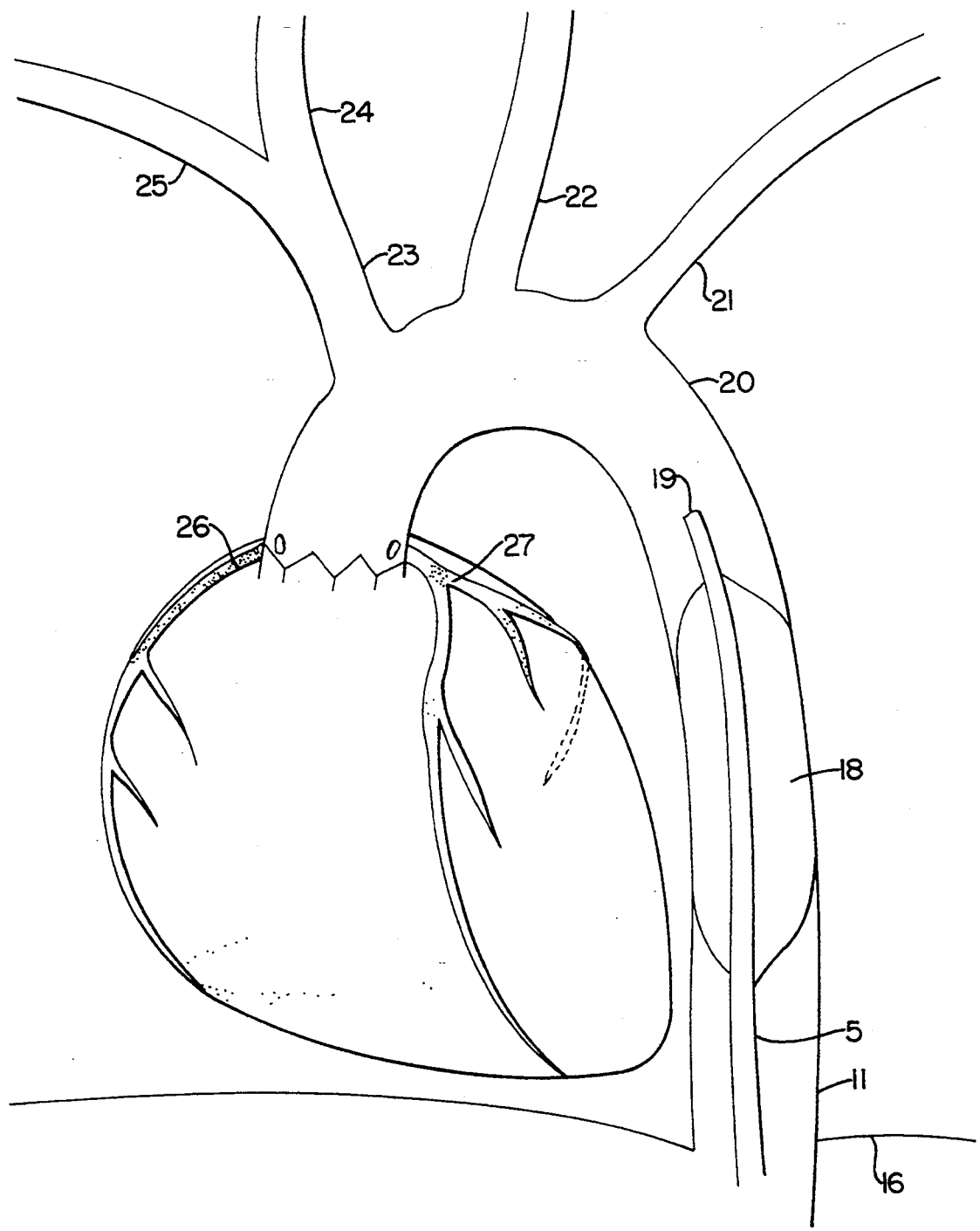
FIG. 2 is an enlarged view of that portion of FIG. 1 showing the balloon catheter positioned to block the descending aorta and perfuse the aortic arch.

As illustrated in FIGS. 1 and 2, a balloon catheter 5 is inserted through the left femoral artery 10 of a human subject, up into the descending aorta 11, past the renal arteries 12, 13, the superior mesenteric artery 14, the celiac trunk 15, through the diaphragm 16, and past various ones of the intercostal arteries 17. The balloon 18 is inflated to block the descending aorta, with the tip of the catheter 19 positioned to perfuse the aortic arch 20. In this position, protective solution pumped or forced through the catheter will perfuse the left subclavian artery 21, the left common carotid artery 22, the brachiocephalic trunk 23 (and through it the right carotid artery 24 and the right subclavian artery 25) and the coronary arteries 26, 27.

The balloon catheter itself comprises an elongate tube having a primary lumen through which the protective solution may pass, and a balloon at one end thereof configured to be inflated to block the descending aorta of a human subject. A second tube, or a secondary lumen formed in the wall of the first tube and extending longitudinally therewith, provides a means for inflating the balloon once the balloon is positioned in the desired location. A connector such as a Leur Lock TM fitting is provided at the end of the elongate tube opposite the balloon to provide a means for connecting the catheter to a supply for the protective solution. For a human adult, the primary lumen size may be from 8 French to 12 French, the catheter length may be from 60 to 100 centimeters, the balloon inflated dimensions may be from 1.5 to 4 centimeters in diameter, the balloon length may be from 2 to 10 centimeters, and the catheter tip to balloon distance may be from 1 to 4 centimeters. For a human child, the lumen size may be from 5 French to 10 French, the catheter length may be from 40 to 80 cm, the balloon inflated dimensions may be from 0.75 to 2 cm in diameter, the balloon length may be 1.5 to 6 cm, and the catheter-tip to balloon distance may be from 0.5 to 2 cm. The balloon, when inflated, should be capable of withstanding at least 300 to 500 mmHg to prevent leakage of protective solution down the descending aorta, and to prevent rupture of the balloon during chest compression. The elongate tube may be made from a firm but somewhat flexible plastic material, and the balloon from a latex or polyurethane material. The catheter may be made from antithrombotic materials, such as having heparin bonding as a characteristic of construction, to inhibit formation of blood clots in the aorta. Reference may be made to U.S. Pat. Nos. 5,049,132; 5,049,131; 5,045,061; 5,042,976; and 5,041,125 for further guidance in the construction of the balloon catheter. It is specifically intended that the disclosures of all patent references cited herein be incorporated herein by reference.

The protective solution is an oxygen-carrying solution (i.e., a perfluorochemical solution, a lactated Ringer's solution, or other blood substitute), optionally containing various other agents such as antioxidants, calcium channel blockers, iron chelators, metabolic substrates, adrenergic agents, etc., in an amount to combat tissue reperfusion injury and/or enhance cardiac activity while protecting the brain until spontaneous circulation is restored. The solution may be a single phase solution, a dispersion, an emulsion, or any other form physically suitable for delivery to the tissue. The protective solution is "physiologically acceptable" in that it is suitable for injection into the subject without causing undue deleterious effects.

Any physiologically acceptable perfluorochemical blood-substitute solution may be employed in carrying out the invention. One example is Fluosol-DA20%, an intravascular perfluorochemical emulsion comprised of 20% perfluorochemical and available from the Alpha Therapeutics Corp. Pasadena, Calif., USA. Aqueous emulsions containing fluorochemicals in high concentration are disclosed in U.S. Pat. Nos. 4,895,876 and 4,866,096; a liquid composition containing perfluorocyclocarbon and an organoamine oxide is disclosed in U.S. Pat. No. 4,443,480; a process for preparing stable emulsions of artificial blood containing perfluoro compounds is disclosed in U.S. Pat. No. 4,497,829; liquid compositions containing fluorinated triethylenediamines are disclosed in U.S. Pat. No. 4,814,446.

The protective solution is oxygenated prior to infusion with an oxygen-rich atmosphere such as Carbogen (95% $O_2$/5% $CO_2$). The protective solution may be administered at ambient temperature, or may be warmed to a temperature up to body temperature (37° Centigrade) prior to administration. The protective solution may further contain a vasoconstrictor, as discussed below. In a human adult, the perfusing step is carried out by perfusing the aortic arch of the subject with from 250 to 2000 milliliters of the protective solution, or more typically from 500 to 1500 milliliters of the protective solution. The infusion step should be carried out sufficiently rapid to enhance cardiac electrical activity, with the perfusion step generally being carried out within five minutes, and more typically within one to two minutes. In general, the rate of infusion will be from 5 to 20 ml/Kg/minute, and will most preferably be from 10 to 15 ml/Kg/minute. The rate of infusion may be uniform throughout the infusion step or may vary through the infusion step. For example, the rate of infusion may be more rapid during the early part of the infusion step to provide an initial bolus of protective solution, followed by a less rapid period of infusion.

Any vasoconstrictor may be employed in the methods described herein, including epinephrine, norepinephrine, methoxamine, phenylephrine, and other alpha adrenergic receptor agonists. Epinephrine is currently preferred. Vasoconstrictors may be administered by any suitable means, such as by parenteral injection (e.g., intravenous injection, intraarterial injection, subcutaneous injection, intramuscular injection, intraperitoneal injection, tracheobronchial administration), or by including the vasoconstrictor in the protective solution used to perfuse the aortic arch. It is preferred that the administration of the vasoconstrictor be concurrent with (i.e., sufficiently close in time to) perfusion of the aortic arch so that the vasoconstrictor will affect coronary perfusion with the protective solution. The dosage of the vasoconstrictor will vary depending on the subject and the particular vasoconstrictor chosen, but will generally be between 0.01 and 0.3 mg/Kg, will more preferably be between 0.02 and 0.2 mg/Kg, and will most preferably be between 0.04 and 0.1 mg/Kg.

Medicaments containing a vasoconstrictor for enhancing coronary perfusion with a protective solution during selective aortic arch perfusion may be prepared by contacting and mixing the vasoconstrictor with a pharmaceutically acceptable carrier, such as a sterile pyrogen-free saline solution, in accordance with techniques known in the pharmacy art. The pharmaceutical carrier may be the protective solution itself, such as a perfluorochemical blood-substitute solution as discussed above.

The step of restoring spontaneous circulation in the subject may be carried out by any suitable means, such as electric shock or precordial thump (i.e., application of an external force), or by enhancing electrical activity through perfusion and other resuscitation techniques so that normal electrical activity re-emerges without application of an external force. An electric shock to heart muscle tissue which will restore spontaneous circulation from a chaotic electrical signal (or "defibrillation") may be administered with any suitable defibrillator, such as the Responder TM 1500, manufactured by Marquette Electronics, 8200 W. Tower Ave., Milwaukee, Wisc. 53223 USA (tel. no. (414) 355-5000).

Invasive techniques such as OCCM, DMVA, and CPB have clearly been shown to provide better vital organ perfusion and improve survival in laboratory studies. However, these techniques are presently limited to the in-hospital setting and they have thus far not been shown to improve longterm survival in out-of-hospital cardiac arrest. See E. Geehr and P. Auerbach, *Ann. Emerg. Med.* 14, 499 (1985); G. Martin et al., *Ann. Emerg. Med.* 19, 480 (1990). Selective aortic arch perfusion is an invasive technique that can be adapted for widespread use in the pre-hospital as well as the emergency department setting. Isolation of the aortic arch with a balloon occlusion catheter allows selective delivery of a specialized solution to the heart and brain by preventing distal aortic flow. Blocking of the left and/or right subclavian arteries by means such as the inflation of pressure cuffs on both upper arms would further limit nonvital organ flow. Even if SAAP is not successful in the field or in the emergency department, it might preserve the heart and brain sufficiently to allow for successful ROSC using other invasive techniques, such as CPB. The catheter could also be designed to interface with an intra-aortic balloon pump to provide diastolic pressure support during the early post-resuscitation phase.

The experimental details set forth below are provided to further illustrate the present invention, and are not to be taken as restrictive thereof.

EXPERIMENTAL

MATERIALS AND METHODS

Description of the technique—Selective aortic arch perfusion (SAAP) involves the insertion of a large-lumen balloon occlusion catheter into the descending aortic arch via a femoral artery. Inflation of the balloon prevents flow into the distal aorta. An oxygenated resuscitation solution is then infused mechanically into the isolated aortic arch, thus providing heart and brain perfusion for a brief time.

Catheter description—Catheters 55 cm in length with 2.7 mm internal diameters and 50 ml balloons withstanding 300 mmHg were created in our laboratory using plastic tubing, glue, suture, and liquid latex.

Animals—Mongrel dogs weighing 21 to 36 kg were used. The experimental protocols were approved by the Institutional Animal Care and Use Committee at the UNC-Chapel Hill School of Medicine.

Anesthesia—Induction with sodium thiopental 25-30 mg/kg was followed by intubation and inhalational ethrane at 1.0-1.5 MAC via a volume ventilator with an $F_IO_2$ of 0.21. Minute ventilation was adjusted to yield an end-tidal $CO_2$ of 38-42 mmHg and ECG lead II was monitored.

Instrumentation—Right external jugular vein and bilateral femoral vessel cutdowns were performed. Micromanometer-tipped catheters (Millar Instruments) were advanced from one femoral artery and vein to the mid-aortic arch and right atrium, respectively. The SAAP catheter was advanced from the other femoral artery to the descending aortic arch, and positioned essentially as shown in FIG. 1. A pacing-port Swan-Ganz catheter (Edwards Laboratory) was advanced from the right external jugular vein into a pulmonary artery. A pacing wire was inserted through the pacing-port into the right ventricle. All catheters were positioned using fluoroscopy. The ECG and pressures were recorded on a multichannel recorder (Grass Instruments Model 7 Polygraph). The OXYPHEROL TM solution was oxygenated prior to infusion by recirculating the solution through a covered graduated cylinder under a 100% $O_2$ atmosphere and pumped into the animal with a SARNS low pressure bypass pump. In Group I only, an electromagnetic flow probe (Carolina Medical Electronics) was placed on the left common carotid artery via a cutdown.

Experimental protocol—After baseline measurements of heart rate, aortic arch pressure (AoP), right atrial pressure (RAP), and left common carotid flow (LCCF), ventricular fibrillation (VF) was induced using the pacing wire and an AC current generator. After ten minutes of VF without any resuscitative efforts, the SAAP catheter balloon was inflated with 40 ml of air (250-300 mmHg) and an experimental solution was infused into the aortic arch using a Sarns low-pressure perfusion pump. There were no other resuscitative efforts used during the infusion period. Three groups of animals received the following infusions in series:

Group I—Six animals (21-36 kg) received approximately 30 ml/kg/min of 0.9% NaCl (23°-25° C.) for two minutes (1500 ml for a 25 kg dog).

Group II—Four animals (24-26 kg) received approximately 30 ml/kg/min of oxygenated lactated Ringer's (23°-25° C.) containing epinephrine 2 mg/l for two minutes followed by CPR (1500 ml and 3 mg epinephrine for a 25 kg dog).

Group III—Four animals (26-29 kg) received approximately 20 ml/kg/min of an oxygenated 20% perfluorochemical solution (OXYPHEROL TM, Alpha Therapeutic Corporation, Los Angeles, Calif.) containing epinephrine 4 mg/l (23°-25° C.) over one minute followed by CPR. (500 ml and 2 mg of epinephrine).

CPR compression rate was 120 min$^{-1}$ with a 5:1 compression:ventilation ratio and 100% oxygen was used. Intravenous contrast was injected into the aortic arch in the first two animals in Group I to confirm balloon occlusion of the aorta.

AoP, RAP, and coronary perfusion pressure [CPP =AoP−RAP] were compared at 10 second intervals during infusion in all groups and during CPR in Groups II and III. VF amplitude (average of the five greatest peak-to-trough deflections over ten seconds, mm) was measured at the onset of VF, after 10 minutes of VF, at the end of infusion, and after one minute of CPR in Groups II and III. In Group I, digital LCCF was recorded before arrest and at 10 second intervals during infusion.

Statistical Analysis—Pressure data during the infusion were compared to pre-infusion using a paired data t-test for each group individually. All data comparisons between groups were done using univariate and multivariate repeated measures analysis of variance. (SAS/STAT Guide for Personal Computers, Version 6 Edition. SAS Institute Inc., Cary, N.C,, USA). A p-value of <0.05 was considered statistically significant.

RESULTS

Pre-arrest hemodynamic parameters were similar for all groups. Infusion rates were 30±5 ml/kg/min for Group I, 32±2 ml/kg/min for Group II, and 19±1 ml/kg/min for Group III. Baseline AoP, RAP, and CPP (mmHg±SD) just prior to aortic infusion were, respectively: 5±4, 3±4, 3±3 3 for Group I; 7±3, 3±5, 4±7 for Group II; and 8±2, 5±4, 4±3 for Group III, (p=NS). The hemodynamic data listed in Table 1 represent the changes in these pressures over baseline during the aortic infusions.

TABLE 1

PRESSURE CHANGES DURING SELECTIVE AORTIC ARCH PERFUSION

|           | 10 sec    | 20 sec    | 30 sec    | 60 sec    | 90 sec    | 120 sec    |
|-----------|-----------|-----------|-----------|-----------|-----------|------------|
| GROUP I   |           |           |           |           |           |            |
| AoP       | 18 ± 11   | 21 ± 13   | 23 ± 11   | 30 ± 9    | 39 ± 10   | 46 ± 12    |
| RAP       | 5 ± 1     | 9 ± 1     | 13 ± 2    | 24 ± 6    | 34 ± 9    | 41 ± 11    |
| CPP       | 14 ± 12   | 12 ± 13   | 10 ± 10   | 6 ± 7     | 6 ± 6     | 5 ± 4      |
| GROUP II  |           |           |           |           |           |            |
| AoP       | 21 ± 5    | 40 ± 6    | 53 ± 6*   | 69 ± 5*   | 87 ± 7*   | 103 ± 9*   |
| RAP       | 4 ± 1     | 8 ± 2     | 13 ± 3    | 29 ± 5    | 47 ± 9    | 61 ± 11**  |
| CPP       | 17 ± 7    | 32 ± 6    | 40 ± 4*   | 40 ± 4*   | 40 ± 4*   | 42 ± 4*    |
| GROUP III |           |           |           |           |           |            |
| AoP       | 19 ± 9    | 39 ± 20   | 54 ± 22*  | 72 ± 21*  | —         | —          |
| RAP       | 2 ± 1**   | 6 ± 2**   | 8 ± 2*#   | 17 ± 2*#  | —         | —          |
| CPP       | 16 ± 10   | 33 ± 22   | 46 ± 24*  | 55 ± 20*# | —         | —          |

All data: mmhg ± SD
*P < 0.005, vs I
**P < 0.05, vs I
P < 0.05, vs II

Significant increases in AoP occurred by 10 seconds of aortic infusion in all groups (p <0.05). RAP also rose significantly in each group (p <0.05). CPP increases were modest in Group I and even trended downward after the initial 20 seconds of infusion as RAP rose.

Figure 3:
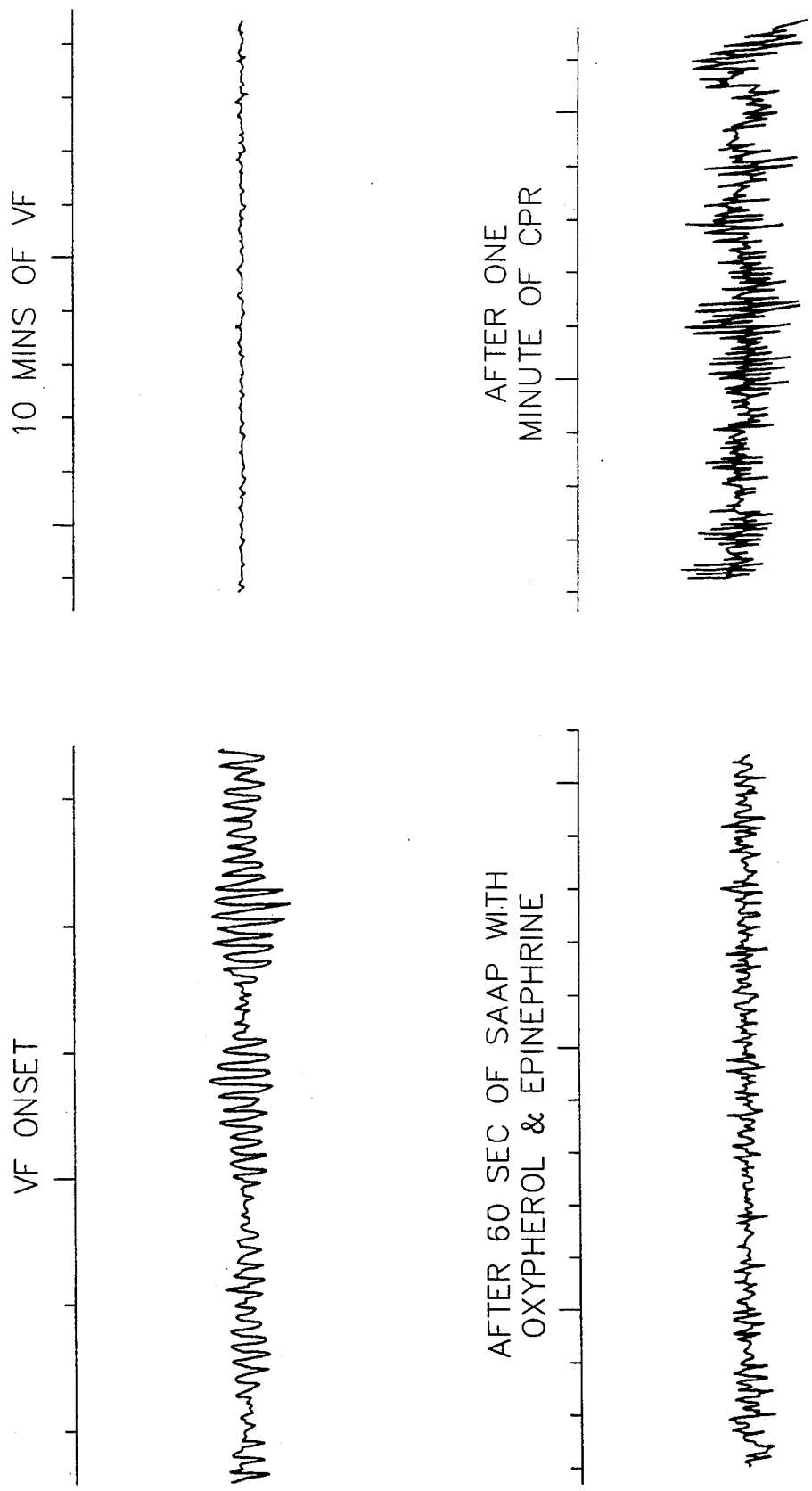
FIG. 3 is a representative electrocardiogram (ECG) tracing of a subject at the onset of ventricular fibrillation (VF), then after ten minutes of VF, then after 60 seconds of selective aortic arch perfusion (SAAP) with an oxygenated perfluorochemical blood substitute solution containing epinephrine, and then after one minute of cardiopulmonary recucitation (CPR). Note the restoration of electrical activity by SAAP, then CPR. Markings on the time tracing above the ECG tracings indicate one second intervals.

FIG. 3 provides a representative electrocardiogram (ECG) tracing of a subject at the onset of ventricular fibrillation (VF), then after ten minutes of VF, then after 60 seconds of selective aortic arch perfusion (SAAP) with an OXYPHEROL ™ solution containing epinephrine, and then after one minute of cardiopulmonary resuscitation (CPR). Markings on the time tracing above the ECG tracings indicate one second intervals. It can be seen that, at the onset of VF, electrical activity is at a level where restoration of spontaneous circulation by defibrillation is likely. After ten minutes of VF, however, electrical activity has been reduced to the point where restoration of spontaneous circulation is unlikely. After one minute of SAAP, however, cardiac electrical activity has been noticably enhanced, and when this is followed by one minute of CPR electrical activity is seen to have been further enhanced.

Figure 4:
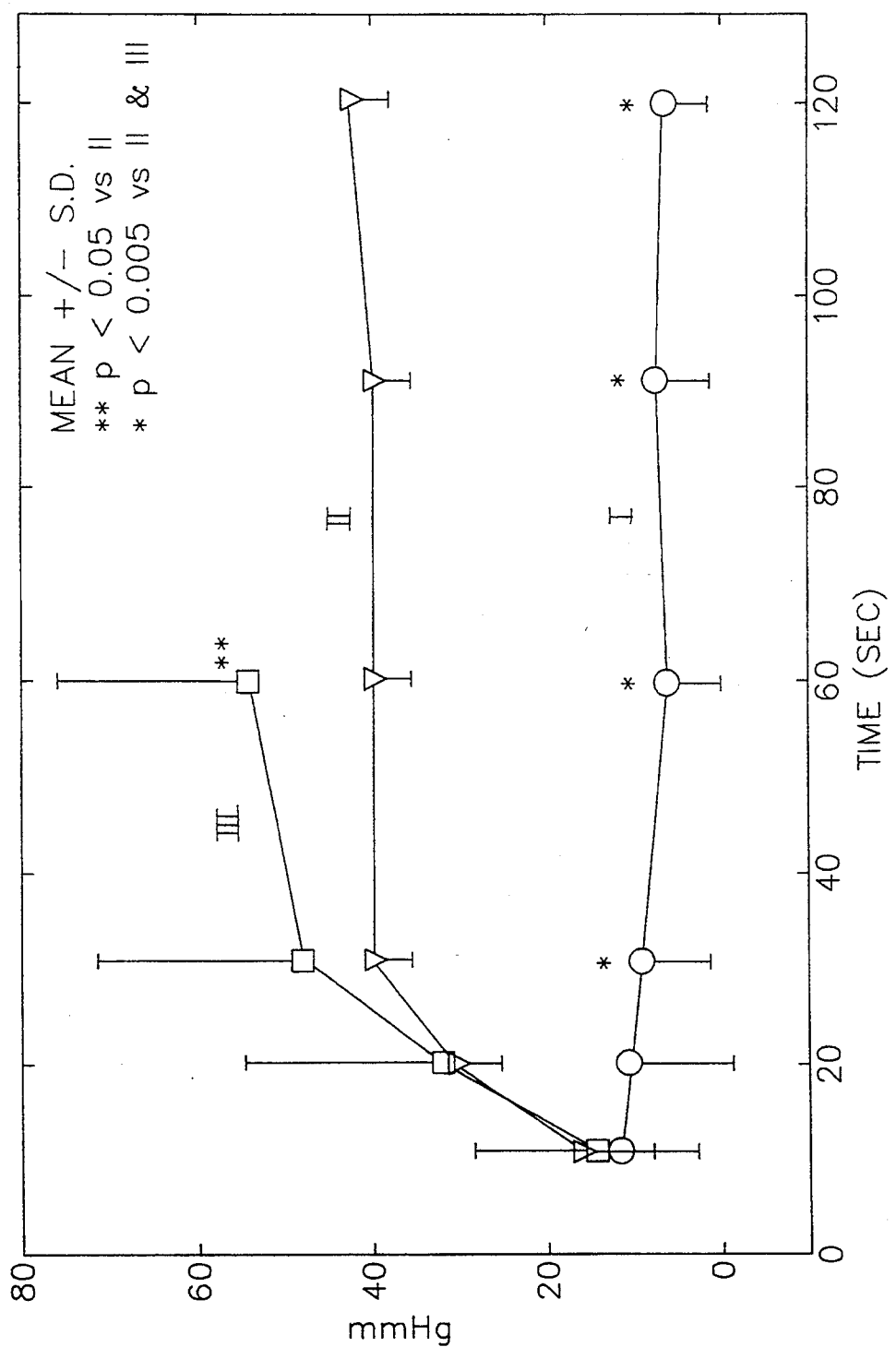
FIG. 4 illustrates the increase in coronary perfusion pressure obtained during selective aortic arch perfusion with concurrent administration of a vasoconstrictor.

The addition of epinephrine in Groups II and III resulted in significantly greater increases in CPP compared to Group I (FIG. 4). However, RAP increases were similar in Groups I and II throughout most of the two minute infusion period. Though AoP increases were similar between Groups II and III, the rise in RAP was not as great in Group III. This resulted in a significantly greater increase in CPP in Group III versus Group II at the 60 second mark of infusion. After 60 seconds of CPR, CPR-diastolic AoP, RAP, and CPP (mmHg±SD) were, respectively: 62±4, 26±6, 36±5 for Group II and 70±24, 14±5, 56±20 for Group III (p <0.05 for RAP only, Group II versus III). All animals in Groups II and III were successfully defibrillated into organized electrocardiographic rhythms. VF amplitude (percent of VF onset±SD) at pre-infusion, post-infusion, and post-CPR were, respectively: 25±11%, 62±9%, 97±10% for Group II and 19±14%, 54±27%, 99±39% for Group III (p=NS, II versus III). LCCF readings were highly variable, but averaged 34–60% of pre-arrest values over the infusion in Group I. There was minimal leak past the balloon in the two Group I animals with aortic contrast injection.

These data demonstrate the feasibility of selective aortic arch perfusion. The significant increases in AoP and RAP during infusion demonstrate successful aortic arch pressurization and arterial-to-venous flow. The small CPP gradients despite good flow in Group I demonstrate the profound vasodilation associated with prolonged cardiac arrest. In Groups II and III, epinephrine resulted in a rapid and marked increase in CPP during infusion and afterwards with CPR to levels that have been noted to correlate with successful resuscitation. See N. Paradis et al., JAMA 263, 1106–1113 (1990). Observations are consistent with the known alpha-adrenergic vasoconstrictor effects of epinephrine during CPR. See C. Brown and H. Werman, Resuscitation 19, 1–16 (1990). Optimal effects on CPP occurred after 0.04–0.08 mg/kg of epinephrine had been infused. Aortic arch administration of vasoconstrictors may prove to be the most rapid, titratable, and effective means of restoring adequate peripheral vascular resistance. They could be administered via the SAAP catheter either in addition to or as a component of the resuscitation solution. The VF amplitude recovery seen in Groups II and III is suggestive that SAAP might enhance ROSC.

The 30 ml/kg/min infusion rate used in Groups I and II was chosen as a rough estimation of normal aortic arch blood flow. The choice of a two minute infusion was arbitrary. The data from Groups I and II suggest that this infusion rate may be greater than optimal. The addition of epinephrine in Group II did not prevent the very large increases in RAP noted in Group I and pulmonary edema was noted consistently during CPR. The less aggressive volume infusion used in Group III (20 ml/kg/min for one minute) resulted in significantly lower RAP while attaining similar AoP and better CPP. However, signs of pulmonary congestion were still seen. The current optimal infusion rate is thus be lower, on the order of 10–15 ml/kg/min, to avoid deleterious right heart pressures and pulmonary edema.

The foregoing examples are illustrative of the present invention, and are not to be construed as limiting thereof. The invention is defined by the following claims, with equivalents of the claims to be included therein.

I claim:

1. A method of treating a subject in cardiac arrest, comprising:

blocking the descending aorta of said subject; and then perfusing the aortic arch of said subject with an oxygen-carrying protective solution in an amount effective to deliver oxygen to the heart of said subject, and concurrently administering said subject an alpha adrenergic receptor agonist in an amount effective to enhance coronary perfusion with said protective solution;

and wherein said perfusing step is carried out by infusing an initial bolus of protective solution, followed by a less rapid infusion of protective solution.

2. A method according to claim 1, wherein said administering step is carried out by parenteral injection.

3. A method according to claim 1, wherein said administering step is carried out by including said alpha adrenergic receptor agonist in said protective solution during said prefusing step.

4. A method according to claim 1, wherein said perfluorochemical solution comprises an emulsion.

5. A method according to claim 1, wherein said alpha adrenergic receptor agonist is selected from the group consisting of epinephrine, norepinephrine, methoxamine, and phenylephrine.

6. A method according to claim 1, wherein said perfusing step is followed by the step of:

restoring spontaneous circulation in said subject.

7. A method according to claim 6, wherein said restoring step is carried out by electric shock.

8. A method according to claim 1, wherein said perfusing step is carried out by perfusing the aortic arch of said subject with from 250 to 2000 milliliters of said protective solution.

9. A method according to claim 1, wherein said perfusing step is carried out for a time of not more than five minutes.

10. A method according to claim 1, wherein said blocking step is carried out with a balloon catheter, and wherein said perfusing step is carried out by administering said protective solution through the lumen of said catheter.

11. A method of treating a subject in cardiac arrest, comprising:

blocking the descending aorta of said subject; and then perfusing the aortic arch of said subject with a perfluorochemical oxygen-carrying protective solution in an amount effective to deliver oxygen to the heart of said subject, and concurrently administering said subject an alpha adrenergic receptor agonist in an amount effective to enhance coronary perfusion with said protective solution;

and wherein said perfusing step is carried out by infusing an initial bolus of protective solution, followed by a less rapid infusion of protective solution.

12. A method according to claim 11, wherein said administering step is carried out by parenteral injection.

13. A method according to claim 11, wherein said administering step is carried out by including said alpha adrenergic receptor agonist in said protective solution during said prefusing step.

14. A method according to claim 11, wherein said perfluorochemical solution comprises an emulsion.

15. A method according to claim 11, wherein said alpha adrenergic receptor agonist is selected from the group consisting of epinephrine, norepinephrine, methoxamine, and phenylephrine.

16. A method according to claim 11, wherein said perfusing step is followed by the step of:

restoring spontaneous circulation in said subject.

17. A method according to claim 16, wherein said restoring step is carried out by electric shock.

18. A method according to claim 11, wherein said perfusing step is carried out by perfusing the aortic arch of said subject with from 250 to 2000 milliliters of said protective solution.

19. A method according to claim 11, wherein said perfusing step is carried out for a time of not more than five minutes.

20. A method according to claim 11, wherein said blocking step is carried out with a balloon catheter, and wherein said perfusing step is carried out by administering said protective solution through the lumen of said catheter.

* * * * *